(12) United States Patent
Bujard et al.

(10) Patent No.: US 6,858,073 B2
(45) Date of Patent: Feb. 22, 2005

(54) PIGMENTED VITREOUS MATERIAL

(75) Inventors: Patrice Bujard, Reinach (CH); Véronique Hall-Goulle, Reinach (CH); Zhimin Hao, Riehen (CH); Hitoshi Nagasue, Nishinomiya (JP); Gerardus De Keyzer, Riehen (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/771,996

(22) Filed: Feb. 4, 2004

(65) Prior Publication Data

US 2004/0159265 A1 Aug. 19, 2004

Related U.S. Application Data

(62) Division of application No. 10/335,727, filed on Jan. 2, 2003, now Pat. No. 6,737,533, which is a division of application No. 09/686,642, filed on Oct. 10, 2000, now Pat. No. 6,524,382.

(30) Foreign Application Priority Data

| Nov. 3, 1999 | (EP) | 99811008 |
| Jul. 4, 2000 | (EP) | 00114313 |

(51) Int. Cl.$^7$ .......................... C03C 14/00; C03C 17/00
(52) U.S. Cl. ................ 106/493; 106/410; 106/411; 106/494; 106/495; 106/496; 106/497; 106/498; 428/1.1; 428/1.62; 428/34.4; 428/426; 501/17
(58) Field of Search ............... 106/410, 411, 106/493, 494, 495, 496, 497, 498, 412; 428/1.1, 1.62, 34.4, 426; 501/17

(56) References Cited

U.S. PATENT DOCUMENTS

| 5,464,566 A | * | 11/1995 | Ito et al. ............... 252/582 |
| 5,484,943 A | | 1/1996 | Zambounis et al. ........ 548/453 |
| 5,502,072 A | | 3/1996 | Masamune ............... 514/418 |
| 5,520,855 A | * | 5/1996 | Ito et al. ............... 252/582 |
| 5,718,998 A | | 2/1998 | Takahashi et al. .......... 430/76 |
| 5,817,832 A | | 10/1998 | Wallquist et al. .......... 548/453 |
| 5,830,267 A | | 11/1998 | Zambounis et al. ........ 106/413 |
| 5,840,449 A | | 11/1998 | Zambounis et al. ........... 430/7 |
| 5,879,855 A | | 3/1999 | Schadeli et al. ......... 430/270.1 |
| 5,973,146 A | | 10/1999 | Rochat et al. ............. 544/144 |
| 6,136,083 A | | 10/2000 | Schmidt et al. ........... 106/403 |
| 6,160,037 A | | 12/2000 | Leugs et al. ............. 523/205 |

FOREIGN PATENT DOCUMENTS

| EP | 504 926 | 6/1995 |
| JP | 03-11357 | 1/1991 |
| WO | 98/32802 | 7/1998 |
| WO | 00/24736 | 5/2000 |
| WO | 00/27930 | 5/2000 |

OTHER PUBLICATIONS

E. Becalli et al., Tetrahedron, vol. 51, No. 8, pp. 2353–2362, (1995), no month.
Chem. Abst. 1997:618422 of JP 09239311 (Sep. 1997).
Chem. Abst. 1998:498069 of JP 10204296 (Aug. 1998).
Chem. Abst. 1995:902719 of JP 07207186 (Aug. 1995).
Chem. Abst. 1996:577084 of JP 08175823 (Jul. 1996).

* cited by examiner

Primary Examiner—Anthony J. Green
(74) Attorney, Agent, or Firm—Tyler A. Stevenson

(57) ABSTRACT

The present application relates to a process for the manufacture of pigmented vitreous materials, as well as to pigmented vitreous materials, characterized by the use of soluble pigment precursors and preferably the absence of significant amounts of dispersants. These pigmented vitreous materials can be used as colored materials for any known purposes. Soluble pigment precursors comprising a partial structure

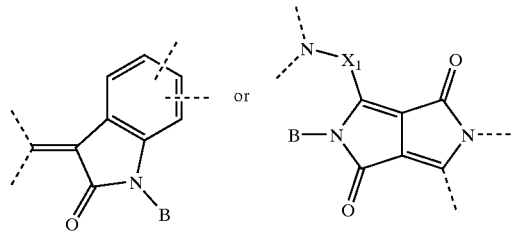

are also claimed, wherein $X_1$ is an aromatic or heteroaromatic ring, B is hydrogen or a group of the formula

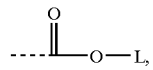

but at least one group B is not hydrogen, and L is a solubilizing group.

26 Claims, No Drawings

PIGMENTED VITREOUS MATERIAL

This is a divisional of U.S. application Ser. No. 10/335,727, filed Jan. 2, 2003, now issued as U.S. Pat. No. 6,737,533, which is a divisional of U.S. application Ser. No. 09/686,642, filed Oct. 10, 2000, now issued as U.S. Pat. No. 6,524,382.

The present application relates to a process for the manufacture of pigmented vitreous materials, as well as to pigmented vitreous materials, characterized by the use of soluble pigment precursors and preferably the absence of significant amounts of dispersants. These pigmented vitreous materials can be used as coloured materials for any known purposes. Examples of uses are layers on beverage bottles, TV screens and other glass items.

As pigmented vitreous materials, there are understood materials comprising a crosslinked matrix of polycondensated transition metal oxides or hydroxides (generally referred to in the literature as "sol-gels"), wherein organic pigment particles are entrapped. The matrix may consist essentially of metal-oxygen-metal links, or may also comprise organic links between the metal atoms. The matrix in particular also can be a hybrid organic-inorganic system, for example an ormocer or a ceramer. All such materials are well-known in the art, and are described for example in many patents and patent applications, such as EP 354 465, EP 426 037, EP 504 926 and EP 590 740, as well as also in reviews articles, reference books and technical encyclopedia.

EP 648 770 and EP 648 817 disclose carbamate-functional, soluble chromophors which can be converted to the corresponding pigments by heating them to relatively high temperatures, with the ensuing elimination of the carbamate radicals. These compounds are suitable for the mass colouring of polymers and, according to EP 654 711, for the colouring of resists and of polymer coats to which they are applied. Compounds of the same type but with improved properties are known for example from EP 742 556, WO 98/32802, WO 98/45757, WO 98/58027 and WO 99/01511.

U.S. Pat. No. 5,243,052 discloses carbonates of quinophthalones, which are of limited solubility and can be used in heat-sensitive recording systems. The leuco dye is embedded within a polymer, preferably in polyethyloxazoline.

EP 504 926 discloses a coating solution composition for forming glass gel thin film, color glass gel filter, and display device using the same, wherein colorant material particles are incorporated together with not less than 0.01 weight % of a dispersant, preferably from 5 to 100 parts by weight with respect to 100 parts by weight of the coloring material. The colorant material particles are such of dyes or pigments, for example azo yellow and red, perylene, perinone, dioxazine, thioindigo, isoindolinone, quinophthalone, quinacridone, phthalocyanine or inorganic pigments. The glass gel thin film is formed at the temperature of 100 to 300° C.

Further, similar sol-gel processes and compositions using organic pigment dispersions are disclosed in JP-A-07/207186, JP-A-08/175823, JP-A-09/239311 and JP-A-10/204296.

The dispersant is disclosed to strengthen the gel film layer, so that the negative influence of the colorant particles would be compensated. However, the sol-gels of the prior art do still not match satisfactory today's high requirements in workability, strength, homogeneity, light, heat and moisture stability, transparency and coloristics. The colorant is not entirely sealed within the inorganic gel, so that it is exposed to oxygen and moisture and partially extracted by chemicals used in the manufacture of articles comprising the gels. High concentrations of colorant furthermore require high amounts of dispersants, leading to further impaired properties. A key limitation is that organic pigments of different classes cannot satisfactory be used together because they require different, often antagonistic dispersants.

The instant invention surprisingly leads to remarkably improved properties through the use of soluble organic pigment precursors which thermally split to insoluble organic pigments. Highly unexpected, the pigment particles are strongly bonded to the gel especially in the absence of an additional dispersant. Surfactants may nevertheless be added, for example to improve the surface quality, but advantageously they are only optional and do not need to be adapted to the pigment. Althought the real mechanism is not elucidated yet, it is believed that the pigment's solubilizing groups do interfere with the gel formation mechanism so that the gel's affinity to organic pigments is improved, instead of just splitting off into an olefin and carbon dioxide as is generally the case in solution.

Hence, the invention relates to a process for making a pigmented vitreous material from a liquid or dissolved transition metal compound, wherein the liquid or dissolved transition metal compound reacts to form crosslinks between the liquid or dissolved transition metal atoms in the pigmented vitreous material, characterized in that the solution also comprises a dissolved compound of the formula $$A(B)_x \qquad (I),$$

in which x is an integer from 1 to 8,

A is the radical of a chromophor of the quinacridone, anthraquinone, perylene, indigo, quinophthalone, indanthrone, isoindolinone, isoindoline, dioxazine, azo, phthalocyanine, diketopyrrolopyrrole or 3-methylidene-2,3-dihydro-indol-2-on series which is attached to x groups B via one or more heteroatoms selected from the group consisting of N, O and S and forming part of the radical A, B is hydrogen or a group of the formula

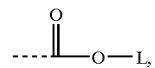

where at least one group B is not hydrogen and, if x is from 2 to 8, the groups B can be identical or different, and L is any suitable solubilizing group, and the vitreous material is heated so that the compound of the formula (I) is transformed into a pigment of the formula $A(H)_x$ (II), in which x has the same meaning as in formula (I).

Transition metals are well-known in the art and may for example be aluminium, zinc, zirconium, titanium, iron, cobalt and nickel, and very particularly silicium. The liquid or dissolved transition metal compounds are also well-known in the art and may for example be an alkoxide or a mixed oxide/alkoxide, which may in addition contain further substituents, for example $C_1$–$C_4$alkyl groups or halogens.

The transformation of the compound of the formula (I) into a pigment of the formula $A(H)_x$ (II) by heating may be performed simultaneously with the liquid or dissolved transition metal compound's crosslinking reaction, or as a separate final step.

Besides the product's excellent properties, the process of the invention has also the advantage that it is much faster than the prior art, due to the fact that a dispersion step is not necessary. Moreover, the reaction can be conducted at higher temperature and at higher pigment contents in the substantial absence of dispersants, without impairing the transparency, hue and chroma.

The reaction is generally performed in the way, that all ingredients are first mixed to form a composition which can be applied as desired and heated to regenerate the pigment. The composition may also contain effective amounts of a catalyst, for example an acid or a precursor which forms an acid upon heating. The acid or precursor may be added at the time of the composition's preparation, or preferably just before the composition's application.

An effective amount of a catalyst is any quantity suitable to start or accelerate the reaction. Catalysts and the suitable quantities thereof are well-known in the art. Examples are mineral acids, such as hydrochloric acid or nitric acid, Lewis acids, such as boron trifluoride, organic acids, such as formic, acetic or oxalic acid, or the like, preferably with a $pK_a$ of 3 or lower.

In addition or even instead of catalysts, it is also well-known to use a light source or to heat the mixture to a mild temperature, for example about 50 to 80° C., in order for the crosslinking reaction (gelation) to start.

Before or during gelation, it is possible to work the composition into the desired form by usual means, for example coating layers by spin coating or by printing methods, such as for example screen or inkjet printing. In analogy to the resist technology (disclosed for example in EP 654 711), it is also possible to perform the crosslinking only in specified areas by using for example a laser or arrays of thermoelements, so that an image is obtained which can be developed for example by washing out the ungelated areas with a suitable solvent.

After the gelation is completed, the material is if necessary further converted to a vitreous form by heating to a higher temperature, at which the pigment will also be regenerated.

The instant pigmented vitreous materials have a high transparency, a high resistance to water, solvent and chemicals as well as also a good resistance to shearing and scratching, and particularly a very high thermal stability even under very severe conditions. Due to their high pigment content, they can be applied in very thin, highly transparent and low scattering layers, the thickness of which is from 0.1 to 3 μm.

The crosslinks between the transition metal atoms may consist for example of oxygen, alkylene, oxyalkylene or oxyalkyleneoxy bridges, which may be unsubstituted or further substituted, for example by oxa or fluoro. Polymeric materials may also be used which have suitable substituents, such as —OH groups, may also be used for crosslinking.

Preferably, the pigmented vitreous material contains each effective pigmenting amounts of from 2 to 10 organic pigments, preferably from 2 to 5 organic pigments.

Suitable solvents are water or, preferably, any desired protic or aprotic solvents, examples being hydrocarbons, alcohols, amides, nitrites, nitro compounds, sulphur derivatives, N-heterocycles, ethers, ketones and esters which may also be either mono- or polyunsaturated or chlorinated: examples are methanol, ethanol, isopropanol, n-butanol, isobutanol, 2-butanol, diethyl ether, acetone, methyl ethyl ketone, methyl isobutyl ketone, 1,2-dimethoxyethane, 1,2-diethoxyethane, 2-n-butoxyethanol, 2-methoxyethanol, 2-ethoxyethanol, ethyl acetate, tetrahydrofuran, dioxane, acetonitrile, benzonitrile, nitrobenzene, N,N-dimethylformamide, N,N-dimethylacetamide, dimethyl sulfoxide, sulfolane, N-methylpyrrolidone, pyridine, picoline, quinoline, dichloroethane, trichloroethane, benzene, toluene, xylene, anisole and chlorobenzene. Further examples of solvents are described in numerous tabular and reference works. Instead of a single solvent it is also possible to employ mixtures of two or more solvents.

The transition metal compounds which undergo crosslinking act themselves as solvents, too. The ratio of transition metal compound to other solvents is preferably from 25:1 to 2.5:1.

The concentration of the pigment precursor in water or a solvent is usually from 0.01% by weight, based on the weight of the solution, to approximately 99% by weight of the saturation concentration, it also being possible in certain cases to employ supersaturated solutions without premature precipitation of the solvate. For many pigment precursors the optimum concentration is around ~0.05–30% by weight, often around 0.1–15% by weight, based on the weight of the solution.

Conversion of the pigment precursor into the pigmentary form takes place by thermal fragmentation, which can be carried out simultaneously with the gel formation or as a subsequent treatment at higher temperature. Thus, the pigment precursor's fragmentation temperature is preferably in the same range as the gel formation, adequately from 50 to 400° C., preferably from 100 to 300° C., most preferably from about 150 to about 250° C.

By an effectively colouring amount is meant that amount which is sufficient to bring about a colour difference $\Delta E^*$ (CIE–L*a*b*) of $\geq 2$ when the pigmented vitreous material is compared with the similarly made, unpigmented vitreous material under the standard illuminant $D_{65}$ and at a viewing angle of 10°. This amount is preferably from 0.01 to about 50% by weight, more preferably from 0.1 to 30% by weight, most preferably from 10 to 25% by weight, based on the weight of the pigmented vitreous material. It is generally preferred to have a pigment concentration as high as possible, without the vitreous material's properties to be impaired.

Judicious fragmentable pigment precursors are those whose structure includes a complete pigment framework substituted on at least one heteroatom N, O or S with an oxycarbonyl radical. Where the heteroatom is part of the chromophor or bonded directly to the chromophor, in the course of fragmentation the oxycarbonyl radical is generally eliminated and replaced by a hydrogen atom, so that the structure of the resulting pigment corresponds to that of the unsubstituted pigment framework. Where, on the other hand, the heteroatom is bonded to a substituent of the chromophor, then the fragmentation process is sometimes more complex, and the precise structure of the resulting pigment cannot always be clearly ascertained.

The pigment precursors can be employed individually or preferably in mixtures with other pigment precursors. Where the pigment precursors are employed in mixtures, the components of the mixture are preferably those whose colour in the pigmentary form is red, blue, yellow, green, orange or black, more preferably bluish red, orange or black.

Bluish red is a wide colour range comprising also colours for which sometimes other designations are used, such as for example magenta, ruby, claret, cabernet, maroon and violet. An especially preferred bluish red has an absorption maximum ($\lambda_{max}$) from 550 to 590 nm, particularly preferred from 560 to 570 nm or from 570 to 580 nm.

Black is preferably a mixture of each a blue and yellow component and from one to 3 red components, especially any mixture of each any C.I. Pigment Blue and Pigment Yellow and any one C.I. Pigment Red or any combination of two or three C.I. Pigment Red and/or Pigment Violet, examples of which are given below. The optimal ratio of the components depends on the respective spectra and should be chosen so that the absorption is nearly the same at all wavelength from 400 to 700 nm, whereby eventual transmission in some areas may be compensated by additional pigments, the absorption maxima of which correspond to the transmission to be reduced.

A preferably contains at least one directly adjacent or conjugated carbonyl group at each heteroatom attached to x groups B.

A is the radical of known chromophores having the basic structure $A(H)_x$. Examples of compounds of formula (I) are known for example from EP 742 556, WO 98/32802, WO 98/45757, WO 98/58027, WO 99/01511, WO 00/17275 and subject-matter of the application PCT/EP-00/03085, as well as from many other publications cited therein, the contents of all are expressly incorporated herein by reference.

Preferred compounds of formula (I) are those disclosed as preferred in WO 98/32802 and WO 98/58027. Particularly noteworthy soluble chromophores of formula (I) are those which can be prepared from Colour Index Pigment Yellow 13, Pigment Yellow 73, Pigment Yellow 74, Pigment Yellow 83, Pigment Yellow 93, Pigment Yellow 94, Pigment Yellow 95, Pigment Yellow 109, Pigment Yellow 110, Pigment Yellow 120, Pigment Yellow 128, Pigment Yellow 139, Pigment Yellow 151, Pigment Yellow 154, Pigment Yellow 175, Pigment Yellow 180, Pigment Yellow 181, Pigment Yellow 185, Pigment Yellow 194, Pigment Orange 31, Pigment Orange 71, Pigment Orange 73, Pigment Red 122, Pigment Red 144, Pigment Red 166, Pigment Red 184, Pigment Red 185, Pigment Red 202, Pigment Red 214, Pigment Red 220, Pigment Red 221, Pigment Red 222, Pigment Red 242, Pigment Red 248, Pigment Red 254, Pigment Red 255, Pigment Red 262, Pigment Red 264, Pigment Brown 23, Pigment Brown 41, Pigment Brown 42, Pigment Blue 25, Pigment Blue 26, Pigment Blue 60, Pigment Blue 64, Pigment Violet 19, Pigment Violet 29, Pigment Violet 32, Pigment Violet 37, 3,6-di(4'-cyanophenyl)-2,5-dihydro-pyrrolo[3,4-c]pyrrole-1,4-dione or 3-phenyl-6-(4'-tert-butyl-phenyl)-2,5-dihydro-pyrrolo[3,4-c]pyrrole-1,4-dione.

Pigment Orange 71 is an especially preferred orange. Pigment Violet 37 is an especially preferred bluish red. Especially preferred black is a mixture of a phthalocyanine blue derivative with Pigment Violet 37, Pigment Yellow 93 or Pigment Yellow 95, and one or more red selected from Pigment Red 222, Pigment Red 254 and 3-phenyl-6-(4'-tert-butyl-phenyl)-2,5-dihydro-pyrrolo[3,4-c]pyrrole-1,4-dione.

Particularly preferred are 3-methylidene-2,3-dihydro-indol-2-on derivatives (such as those disclosed in WO-00/24736 wherein $R_1$ is H), 2,5-dihydro pyrrolo[3,4-c]pyrrole-1,4-dione derivatives having in the 3 and/or 6 position a rest substituted by at least one amino group (such as those disclosed in EP-B-353184 or EP-A-755933), and the β crystal modifications of quinacridones. The contents of WO-00/24736, EP-B-353184 and EP-A-755933 are incorporated herein by reference. These pigments, pure or in combination with other pigments, are particularly suitable for obtaining violet or green colourations. They also lead to surprisingly improved performance in vitreous materials.

When unsubstituted quinacridone is used, then it is preferred that the vitreous materials comprise it in its β crystal modification. As will be shown below, the crystal modification depends on the solubilizing groups and the conditions of regeneration.

Particularly preferred is a 3-methylidene-2,3-dihydro-indol-2-on derivative of the formula

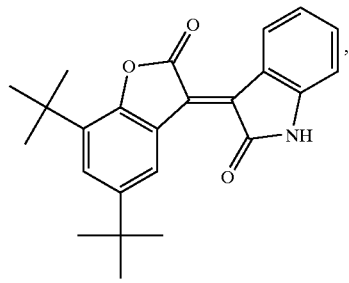

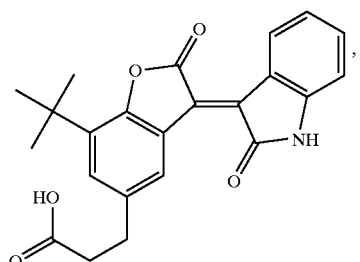

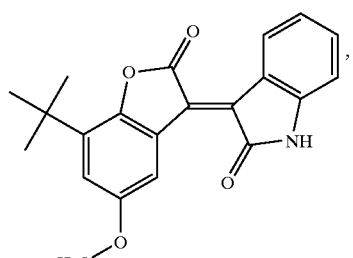

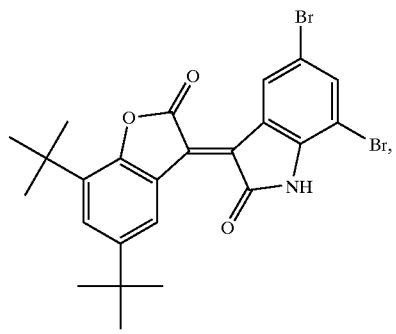

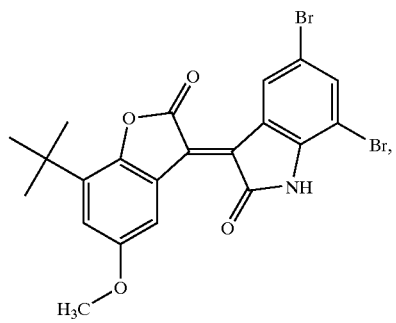

-continued

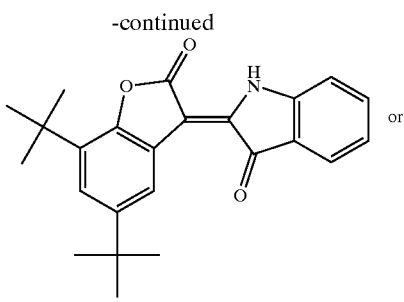

or

Other 3-methylidene-2,3-dihydro-indol-2on derivatives having other substituents are described for example in the above-cited reference WO-00/24736.

Compounds which include at least one

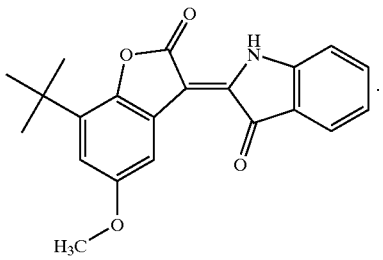

moiety in their structure are new and are also an object of the invention.

Particularly preferred is a 2,5-dihydro-pyrrolo[3,4-c] pyrrole-1,4-dione of the formula

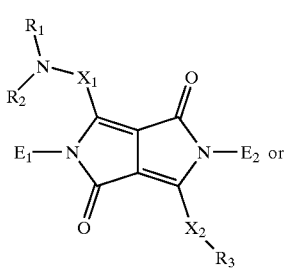

(IIIa)

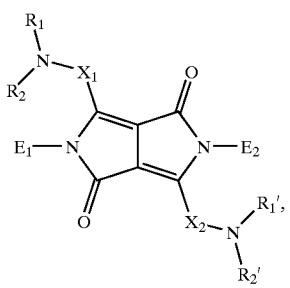

(IIIb)

in which $X_1$ and $X_2$ independently of one another are a divalent aromatic radical of the formula

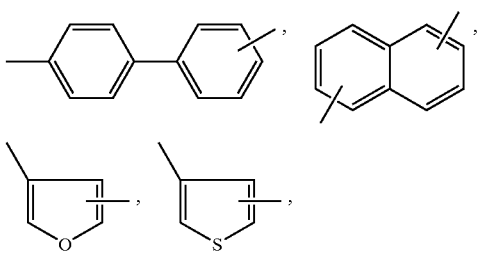

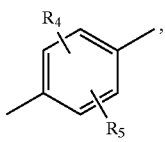

or, most preferably,

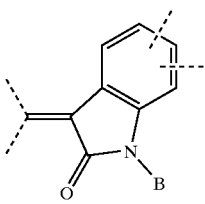

$R_3$ is a radical CN, $COR_6$, $CO_2R_6$, $CON(R_6)_2$, $NO_2$, $SO_2R_6$, $SOR_6$, $SO_2N(R_6)_2$ or $PO(OR_7)_2$, $R_4$ and $R_5$ independently of one another are hydrogen, chlorine, bromine, methyl, ethyl, methoxy or ethoxy, $R_7$ is $C_1$–$C_6$alkyl or phenyl, $R_1$, $R_2$, $R_1'$, $R_2'$ and $R_6$ independently of one another are hydrogen, $C_1$–$C_{18}$alkyl or $C_1$–$C_{18}$alkenyl which is unsubstituted or substituted by hydroxy, mercapto, $C_1$–$C_6$alkoxy or $C_1$–$C_6$alkylmercapto, or phenyl which is unsubstituted or substituted by chlorine, bromine, hydroxy, $C_1$–$C_6$alkyl, $C_1$–$C_6$alkoxy, $C_1$–$C_6$alkylmercapto, CN, $NO_2$ or $CF_3$, or $R_1$ and $R_2$ or $R_1'$ and $R_2'$, together with the nitrogen atom to which they are attached, form a 5- or 6-membered heterocyclic radical which is unsubstituted or substituted by $C_1$–$C_6$alkyl or phenyl and is selected from the group consisting of pyrrolidinyl, piperidyl, pyrrolyl, triazolyl, imidazolyl, pyrazolyl, piperazinyl, morpholinyl, thiomorpholinyl, carbazol-1-yl, indol-1-yl, indazol-1-yl, benzimidazol-1-yl, tetrahydroquinol-1-yl and tetrahydroquin -1-2-yl, or, if $R_1$ or $R_1'$ is hydrogen, $R_2$ or $R_2'$ is a radical of the formula

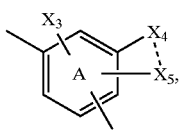

in which $X_3$ and $X_4$ independently of one another are hydrogen, chlorine, bromine, $NO_2$, methyl, methoxy or ethoxy and $X_5$ and $X_6$ form a 5- or 6-membered heterocyclic ring which together with A produces a benzimidazolonyl, dihydroxyquinazolinyl, quinolonyl, benzoxazolonyl, phenmorpholonyl, quinazolinonyl or phthalimidyl radical or a radical of the formula in which $R_6$ is $C_1$–$C_6$alkyl or phenyl,
or $X_2$—$R_3$ can be a radical and $E_1$ and $E_2$ are both hydrogen.

The compounds of formula (IIIa) and (IIIb) wherein $E_1$ is hydrogen and $E_2$ is a group B, $E_1$ is a group B and $E_2$ is hydrogen, or $E_1$ and $E_2$ are both a group B, are new, with exception of such of formula (IIIb) wherein $R_1$ is $C_1$–$C_{18}$alkylamino. The invention also pertains to them.

Particularly preferred quinacridones are unsubstituted quinacridone and the 2,9-, 3,10- and 4,11-isomers of dimethoxyquinacridone, dimethylquinacridone or dichloroquinacridone, especially unsubstituted quinacridone.

The compounds of the formula (I) are known or can be prepared in analogy to methods known per se, as described, for example, in EP 648 770, EP 648 817 and EP 742 556.

Preferably —L is a group of the formula in which $R_1$, $R_3$ and $R_2$ independently of one another are $C_1$–$C_6$alkyl, $R_4$ and $R_5$ independently of one another are $C_1$–$C_6$alkyl, O, S or $N(R_{12})_2$-interrupted $C_1$–$C_6$alkyl, unsubstituted or $C_1$–$C_6$alkyl-, $C_1$–$C_6$alkoxy-, halo-, cyano- or nitro-substituted phenyl or biphenylyl, $R_6$, $R_7$ and $R_8$ independently of one another are hydrogen or $C_1$–$C_6$alkyl, $R_9$ is hydrogen, $C_1$–$C_6$alkyl or a group of the formula $R_{11}$ and $R_{10}$ independently of one another are hydrogen, $C_1$–$C_6$alkyl, $C_1$–$C_6$alkoxy, halogen, cyano, nitro, $N(R_{12})_2$, unsubstituted or halo-, cyano-, nitro-, $C_1C_6$alkyl- or $C_1$–$C_6$alkoxy-substituted phenyl, $R_{12}$ and $R_{13}$ are $C_1$–$C_6$alkyl, $R_{14}$ is hydrogen or $C_1$–$C_6$alkyl and $R_{15}$ is hydrogen, $C_1$–$C_6$alkyl, unsubstituted or $C_1$–$C_6$alkyl-substituted phenyl, Q is p,q-$C_2$–$C_6$alkylene which is unsubstituted or substituted one or more times by $C_1$–$C_6$alkoxy, $C_1$–$C_6$alkylthio or $C_2$–$C_{12}$dialkylamino, p and q being different numeric locants, X is a heteroatom selected from the group consisting of N, O and S, where m is 0 if X is O or S and is 1 if X is N, and $L_1$ and $L_2$ independently of one another are unsubstituted or mono- or poly-$C_1$–$C_{12}$alkoxy-, —$C_1$–$C_{12}$alkylthio-, —$C_2$–$C_{24}$dialkylamino-, —$C_6$–$C_{12}$aryloxy-, —$C_6$–$C_{12}$arylthio-, —$C_7$–$C_{24}$alkylarylamino- or —$C_{12}$–$C_{24}$diarylamino-substituted $C_1$–$C_6$alkyl or [-(p', q'-$C_2$–$C_6$alkylene)-Z—]$_n$—$C_1$–$C_6$alkyl, where n is a number from 1 to 1000, p' and q' are different numeric locants, each Z independently of the others is a heteroatom O, S or $C_1$–$C_{12}$alkyl-substituted N, and $C_2$–$C_6$alkylene in the repeating units [—$C_2$–$C_6$alkylene-Z—] can be identical or different, and $L_1$ and $L_2$ can be saturated or mono- to decaunsaturated, uninterrupted or interrupted in any desired points by from 1 to 10 groups selected from the group consisting of —(C═O)— and —$C_6H_4$—, and may carry no or 1 to 10 further substituents selected from the group consisting of halogen, cyano and nitro.

Of particular interest are compounds of the formula (I) in which L is $C_1$–$C_6$alkyl or particularly $$—Q—\overset{(L_1)_m}{X}—L_2,$$

in which Q is $C_2$–$C_4$alkylene and $L_1$ and $L_2$ are [—$C_2$–$C_{12}$alkylene-Z—]$_n$—$C_1$–$C_{12}$alkyl or are $C_1$–$C_{12}$alkyl which is substituted one or more times by $C_1$–$C_{12}$alkoxy, $C_1$–$C_{12}$alkylthio or $C_2$–$C_{24}$dialkylamino, and m and n are as defined above.

Of very particular interest are compounds of the formula (I) in which L is $C_4$–$C_5$alkyl (especially tert.-butyl or tert.-amyl) or particularly $$—Q—\overset{(L_1)_m}{X}—L_2,$$

in which Q is $C_2$–$C_4$alkylene, X is O and m is zero, and $L_2$ is [—$C_2$–$C_{12}$alkylene-O—]$_n$—$C_1$–$C_{12}$alkyl or is $C_1$–$C_{12}$alkyl which is substituted one or more times by $C_1$–$C_{12}$alkoxy, especially those in which —Q—X— is a group of the formula —C(CH$_3$)$_2$—CH$_2$—O—.

Alkyl or alkylene can be straight-chain, branched, monocyclic or polycyclic.

Thus $C_1$–$C_{12}$alkyl is, for example, methyl, ethyl, n-propyl, isopropyl, n-butyl, sec-butyl, isobutyl, tert-butyl, cyclobutyl, n-pentyl, 2-pentyl, 3-pentyl, 2,2-dimethylpropyl, cyclopentyl, cyclohexyl, n-hexyl, n-octyl, 1,1,3,3-tetramethylbutyl, 2-ethylhexyl, nonyl, trimethylcyclohexyl, decyl, menthyl, thujyl, bornyl, 1-adamantyl, 2-adamantyl or dodecyl.

If $C_2$–$C_{12}$alkyl is mono- or polyunsaturated it is $C_2$–$C_{12}$alkenyl, $C_2$–$C_{12}$alkynyl, $C_2$–$C_{12}$alkapolyenyl or $C_2$–$C_{12}$alkapolyynyl in which two or more double bonds may if appropriate be isolated or conjugated, examples being vinyl, allyl, 2-propen-2-yl, 2-buten-1-yl, 3-buten-1-yl, 1,3-butadien-2-yl, 2-cyclobuten-1-yl, 2-penten-1-yl, 3-penten-2-yl, 2-methyl-1-buten-3-yl, 2-methyl-3-buten-2-yl, 3-methyl-2-buten-1-yl, 1,4-pentadien-3-yl, 2-cyclopenten-1-yl, 2-cyclohexen-1-yl, 3-cyclohexen-1-yl, 2,4-cyclohexadien-1-yl, 1-p-menthen-8-yl, 4(10)-thujen-10-yl, 2-norbornen-1-yl, 2,5-norbornadien-1-yl, 7,7-dimethyl- 2,4-norcaradien-3-yl or the various isomers of hexenyl, octenyl, nonenyl, decenyl or dodecenyl.

$C_2$–$C_4$alkylene is, for example, 1,2-ethylene, 1,2-propylene, 1,3-propylene, 1,2-butylene, 1,3-butylene, 2,3-butylene, 1,4-butylene or 2-methyl-1,2-propylene. $C_5$–$C_{12}$alkylene is, for example, an isomer of pentylene, hexylene, octylene, decylene or dodecylene.

$C_1$–$C_{12}$alkoxy is O—$C_1$–$C_{12}$alkyl, preferably O—$C_1$–$C_4$alkyl.

$C_6$–$C_{12}$aryloxy is O—$C_6$–$C_{12}$aryl, for example phenoxy or naphthoxy, preferably phenoxy. $C_1$–$C_{12}$alkylthio is S—$C_1$–$C_{12}$alkyl, preferably S—$C_1$–$C_4$alkyl.

$C_6$–$C_{12}$arylthio is S—$C_6$–$C_{12}$aryl, for example phenylthio or naphthylthio, preferably phenylthio.

$C_2$–$C_{24}$dialkylamino is N(alkyl$_1$)(alkyl$_2$), where the sum of the carbon atoms in the two groups alkyl$_1$ and alkyl$_2$ is from 2 to 24, preferably N($C_1$-$C_4$alkyl)—$C_1$–$C_4$alkyl.

$C_7$–$C_{24}$alkylarylamino is N(alkyl$_1$)(aryl$_2$), where the sum of the carbon atoms in the two groups alkyl$_1$ and aryl$_2$ is from 7 to 24, for example methylphenylamino, ethylnaphthylamino or butylphenanthrylamino, preferably methylphenylamino or ethylphenylamino.

$C_{12}$–$C_{24}$diarylamino is N(aryl$_1$)(aryl$_2$), where the sum of the carbon atoms in the two groups aryl$_1$ and aryl$_2$ is from 12 to 24, for example diphenylamino or phenylnaphthylamino, preferably diphenylamino.

$C_6$–$C_{16}$aryl ist for example phenyl, naphthyl, anthracenyl, pyrenyl or naphthacenyl.

$C_7$–$C_{24}$aralkyl ist any group comprising at least each an alkyl and an aryl part, for example benzyl, phenethyl, tolyl, dodecylphenyl, indanyl or acenaphtenyl.

Halogen is chlorine, bromine, fluorine or iodine, preferably fluorine or chlorine, most preferably fluorine.

n is preferably a number from 1 to 100, with particular preference a number from 2 to 12.

Particularly preferred pigment precursors are such wherein the chromophore is Colour Index Pigment Yellow 13, Pigment Yellow 73, Pigment Yellow 74, Pigment Yellow 83, Pigment Yellow 93, Pigment Yellow 94, Pigment Yellow 95, Pigment Yellow 109, Pigment Yellow 110, Pigment Yellow 120, Pigment Yellow 128, Pigment Yellow 139, Pigment Yellow 151, Pigment Yellow 154, Pigment Yellow 175, Pigment Yellow 180, Pigment Yellow 181, Pigment Yellow 185, Pigment Yellow 194, Pigment Orange 31, Pigment Orange 71, Pigment Orange 73, Pigment Red 122, Pigment Red 144, Pigment Red 166, Pigment Red 184, Pigment Red 185, Pigment Red 202, Pigment Red 214, Pigment Red 220, Pigment Red 221, Pigment Red 222, Pigment Red 242, Pigment Red 248, Pigment Red 254, Pigment Red 255, Pigment Red 262, Pigment Red 264, Pigment Brown 23, Pigment Brown 41, Pigment Brown 42, Pigment Blue 25, Pigment Blue 26, Pigment Blue 60, Pigment Blue 64, Pigment Violet 19, Pigment Violet 29, Pigment Violet 32, Pigment Violet 37, 3,6-di(4'-cyanophenyl)-2,5-dihydro-pyrrolo[3,4-c]pyrrole-1,4-dione or 3-phenyl-6-(4'-tert-butyl-phenyl)-2,5-dihydro-pyrrolo[3,4-c]pyrrole-1,4-dione, all B are identical groups of the formula

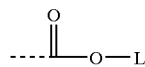

and for each of above chromophores L is tert.-butyl, tert.-amyl, 3-methoxy-2-methyl-2-propyl, 3-(2'-methoxyethoxy)-2-methyl-2-propyl, 2-methyl-3-butin-2-yl or 3-methyl-2-buten-1-yl.

The invention also pertains to a vitreous material comprising a matrix of crosslinked liquid or dissolved transition metal atoms and an effective pigmenting amount of a pigment selected from Colour Index Pigment Yellow 13, Pigment Yellow 73, Pigment Yellow 74, Pigment Yellow 93, Pigment Yellow 94, Pigment Yellow 95, Pigment Yellow 109, Pigment Yellow 120, Pigment Yellow 128, Pigment Yellow 139, Pigment Yellow 151, Pigment Yellow 154, Pigment Yellow 175, Pigment Yellow 180, Pigment Yellow 181, Pigment Yellow 185, Pigment Yellow 194, Pigment Orange 31, Pigment Orange 71, Pigment Orange 73, Pigment Red 144, Pigment Red 166, Pigment Red 184, Pigment Red 185, Pigment Red 202, Pigment Red 214, Pigment Red 220, Pigment Red 221, Pigment Red 222, Pigment Red 242, Pigment Red 248, Pigment Red 255, Pigment Red 262, Pigment Red 264, Pigment Brown 23, Pigment Brown 41, Pigment Brown 42, Pigment Blue 25, Pigment Blue 26, Pigment Blue 60, Pigment Blue 64, Pigment Violet 29, Pigment Violet 32, Pigment Violet 37, 3,6-di(4'-cyanophenyl)-2,5-dihydro-pyrrolo[3,4-c]pyrrole-1,4-dione or 3-phenyl-6-(4'-tert-butyl-phenyl)-2,5-dihydro-pyrrolo[3,4-c]pyrrole-1,4-dione.

In addition to the pigment, the vitreous material may also contain other compounds such as additives known in the art to improve the material's properties such as UV absorbers or transparency improvers.

Heating can be carried out by any desired thermal means, including irradiation; for example, by treatment in a thermal oven or by electromagnetic radiation, for example IR or NIR radiation, or laser pulses or microwaves.

The heating time for regenerating the pigment is not critical, as long as care is taken that it is sufficiently long for the fragmentation of the pigment precursor to be completed. Typically, it ranges from several seconds to several hours, preferably from about 1 to about 30 minutes.

The suitable heating time for gel formation depends on the temperature according to the laws of thermodynamics, so that it can simply be determined depending on the desired temperature.

The heating temperature, however, should be evaluated carefully. In general, it is appropriate to use a temperature from 150 to 300° C., especially from about 180° C. to 250° C. Preferred temperatures are from 180° C. to 200° C. Together with the solubilizing group and the solvent used for gel formation, the temperature influences the crystal structure of the pigment which is formed. Typically, one should run parallel experiments at 150° C. and 200° C. to check for eventual coloristic differences.

Surprisingly, it has been found that the use of a pigment precursor in which L is

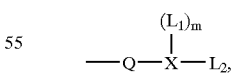

together with a solvent for gel formation of structure

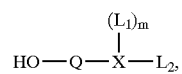

leads to improvements in colour. Especially, this combination enables to get quinacridones in their desired β crystal phase at a temperature of 200° C. or even lower.

Hence, the invention also pertains to a process as defined above, additionally comprising adding a compound of structure

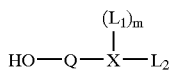

and then heating to a temperature from 150 to 300° C. to form the vitreous material. The compound may be added at once or also in portions, at any time from the beginning to just before the heating step, in any amounts. Preferably, the weight ratio of such compound to compound (I) is from 1:4 to 100:1.

Preferred solvents for gel formation are 2-$C_1$–$C_{12}$alkoxyethanol, 2-$C_1$–$C_{12}$alkoxypropanol, 2,3-di-$C_1$–$C_{12}$alkoxypropanol, diethylenglycol-mono-$C_1$–$C_{12}$alkyl ether, triethylenglycol-mono-$C_1$–$C_{12}$alkyl ether, dipropylenglycol-mono-$C_1$–$C_{12}$alkyl ether, tripropylenglycol-mono-$C_1$–$C_{12}$alkyl ether, or diethylenglycol, triethylenglycol, dipropylenglycol or tripropylenglycol each monoesterified with a $C_1$–$C_{12}$ carboxylic acid.

When a catalyst is used in the form of its precursor, the catalyst precursor can for example be of formula

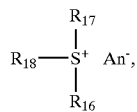 (IVa)

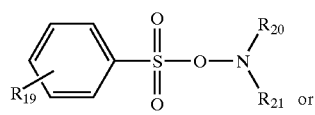 (IVb)

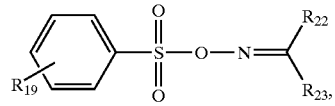 (IVc)

wherein $R_{16}$, $R_{17}$ and $R_{18}$ are independently from one another $C_1$–$C_{24}$alkyl, $C_6$–$C_{24}$aryl or $C_7$–$C_{24}$aralkyl, $R_{19}$ is $C_1$–$C_{24}$alkyl, $R_{20}$, $R_{21}$, $R_{22}$ and $R_{23}$ are independently from one another $C_4$–$C_{24}$alkyl, $C_4$–$C_{24}$aryl or $C_7$–$C_{24}$aralkyl, or $R_{20}$ and $R_{21}$ together or $R_{22}$ and $R_{23}$ together are $C_4$–$C_{24}$alkylen, $C_4$–$C_{24}$aralkyten, 3-oxa-pentylen or N—$C_1$–$C_{24}$alkyl-3-aza-pentylen, An is $PX_6$, $AsX_6$, $SbX_6$, $BX_4$, $R_{24}$—$SO_3$, $R_{24}$—$OSO_3$ or $R_{25}$—$PO_3R_{26}$, wherein $R_{24}$, $R_{25}$ and $R_{26}$ are independently from one another $C_1$–$C_{24}$alkyl, $C_6$–$C_{24}$aryl or $C_7$–$C_{24}$aralkyl. $R_{25}$ and $R_{26}$ are preferably $C_1$–$C_{24}$alkyl, most preferably $C_1$–$C_4$alkyl, particularly methyl, and X is halogen.

Further substituents may be present in the compounds of formulae (IVa), (IVb) and (IVc), for example halogen atoms or nitro or $C_1$–$C_{24}$alkoxy groups.

Of course, the instant new 3-methylidene-2,3-dihydro-indol-2-on and amino-substituted2,5-dihydro-pyrrolo[3,4-c]pyrrole-1,4dione colorants may also be used in other fields, for example as fluorescent colorants or as latent pigments, such as described for example in U.S. Pat. No. 5,484,943, EP-B-0 648 817, U.S. Pat. No. 5,879,855, WO98/45756, WO98/45757, WO98/58027, WO00/27930 and EP application 99810467.3.

The examples which follow illustrate the invention, without limiting its scope in any way.

---

Structures of soluble pigment precursors:

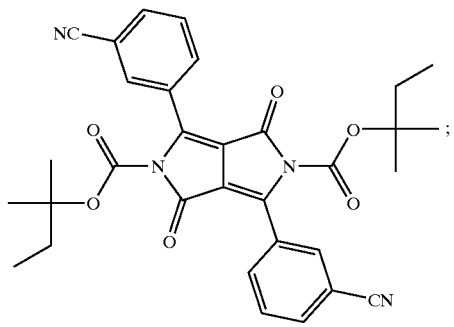 (A1)

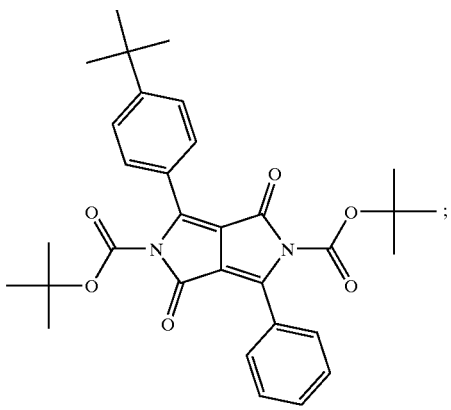 (A2)

-continued
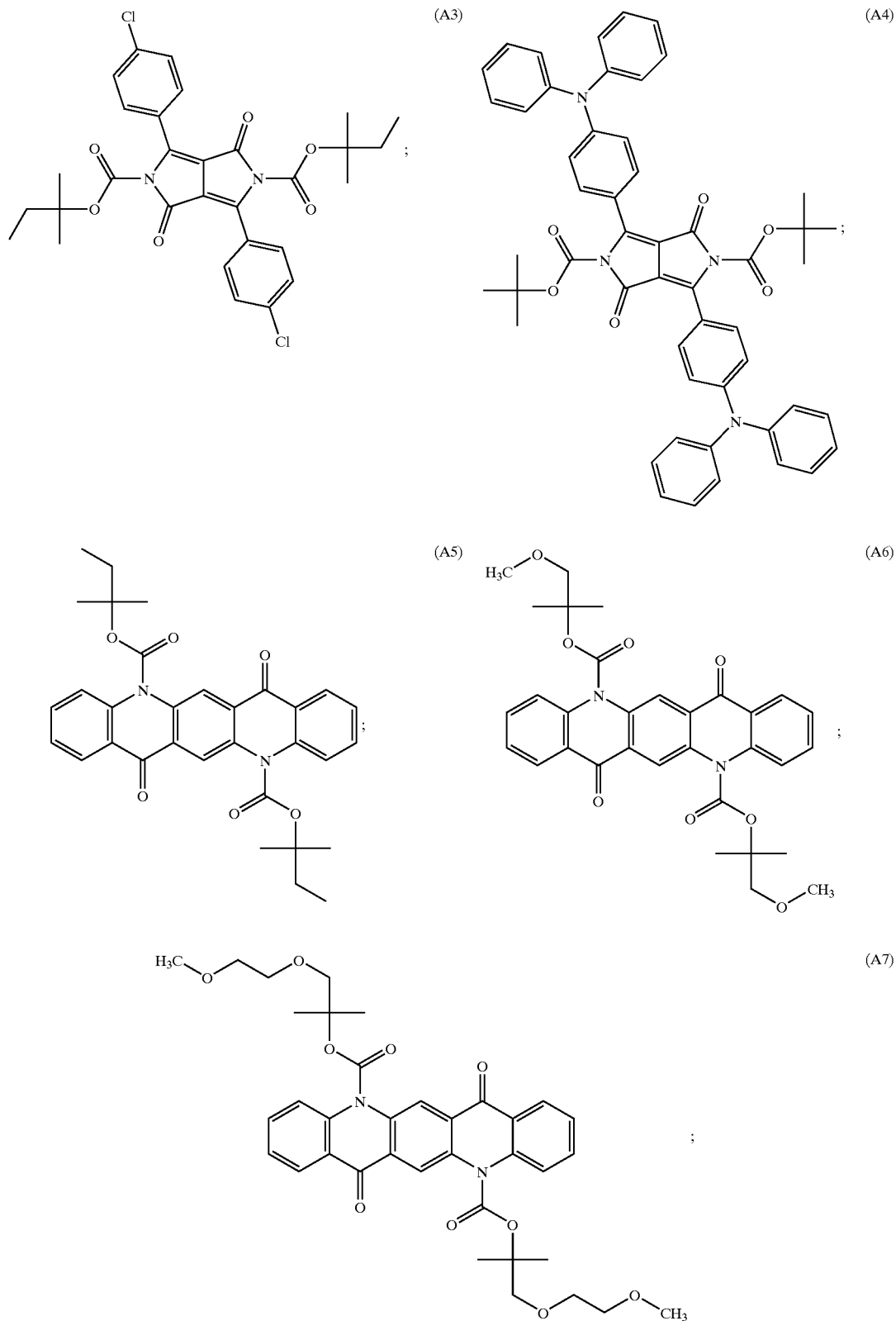

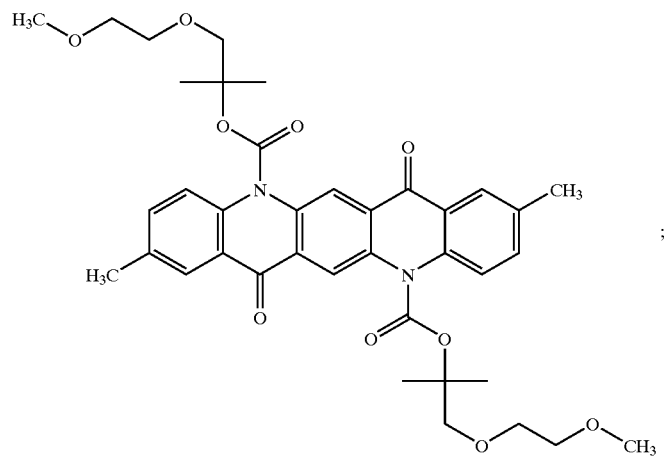
(A8)
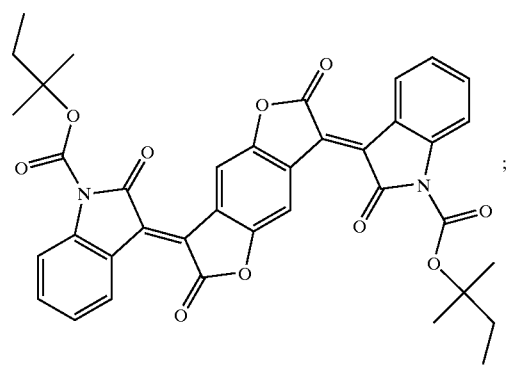
(A9)
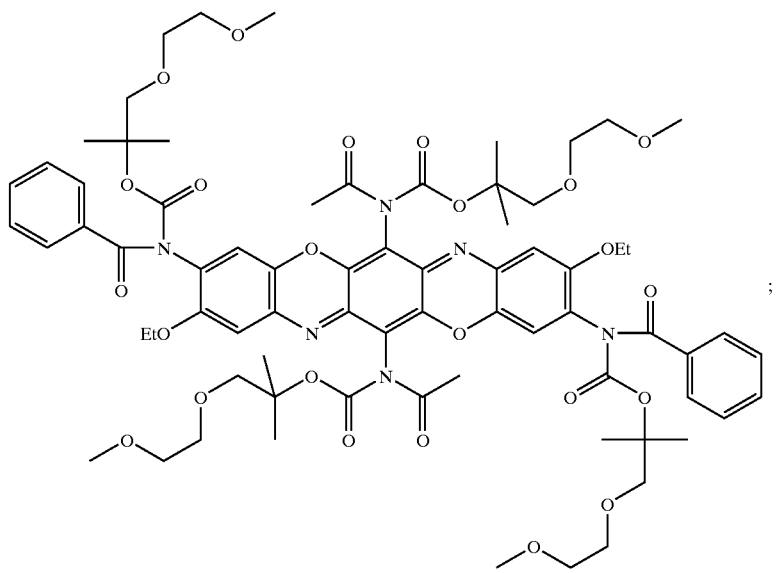
(A10)

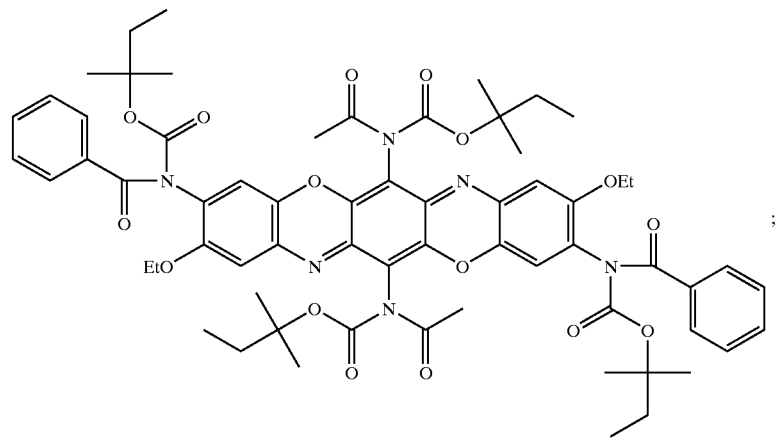
(A11)
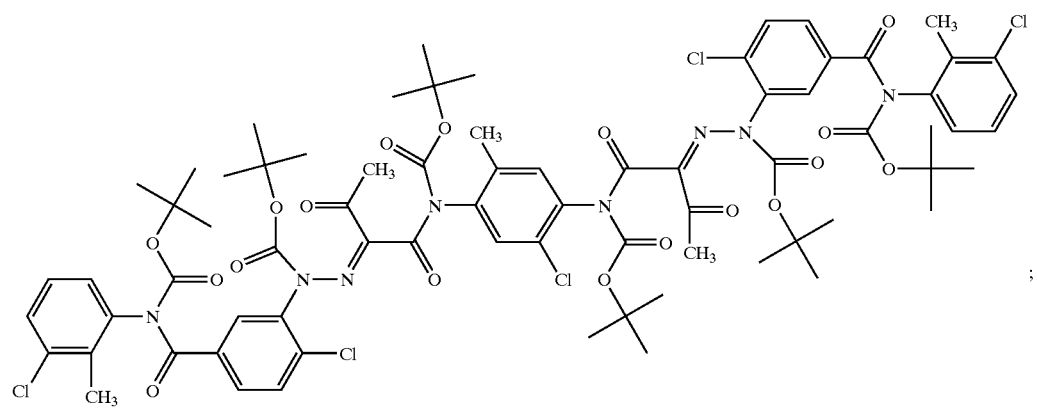
(A12)
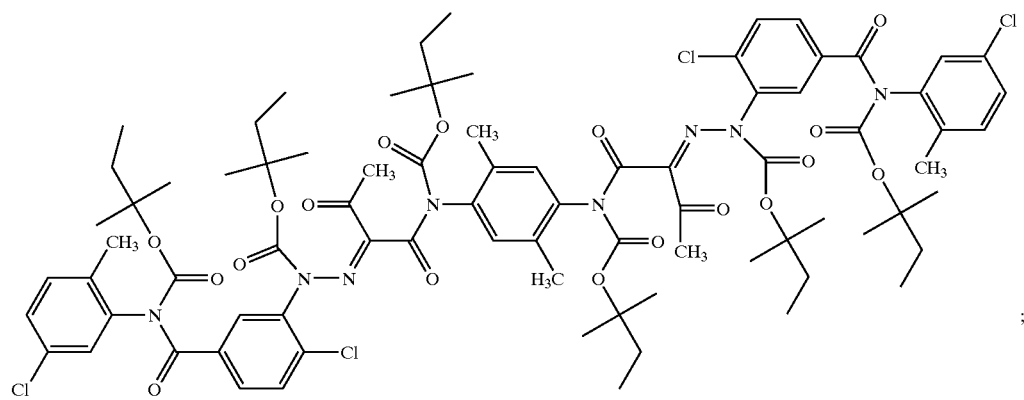
(A13)

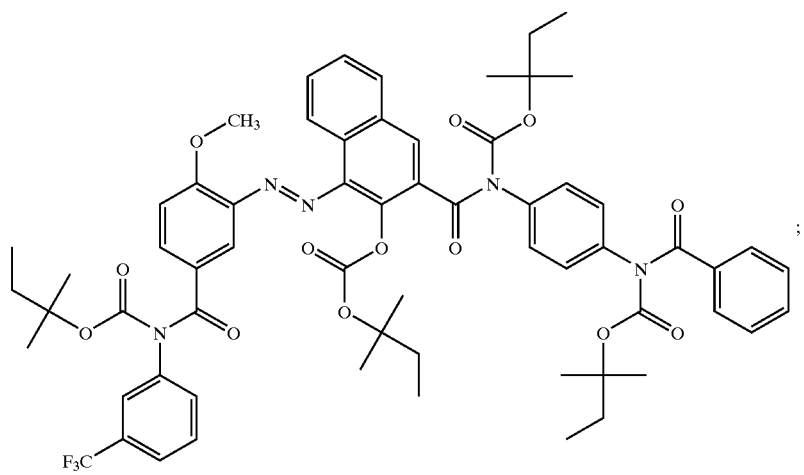
(A14)
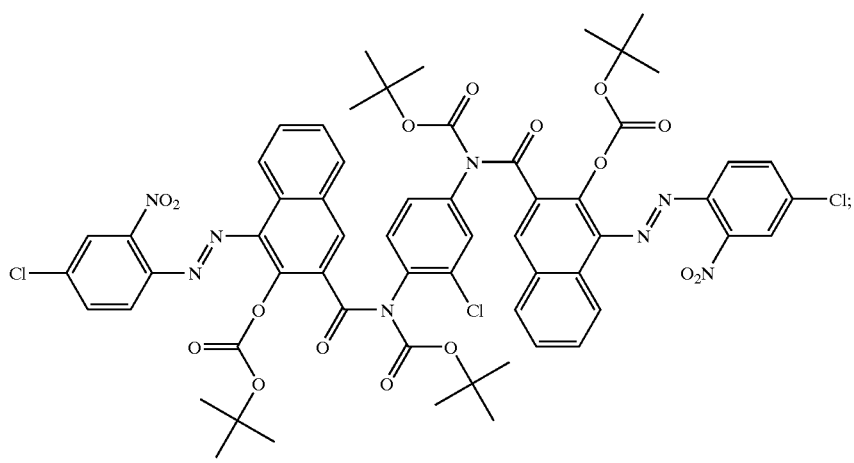
(A15)
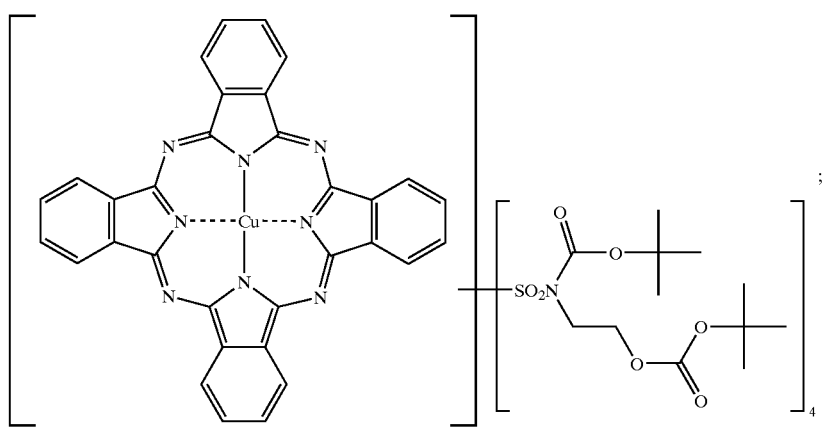
(A16)

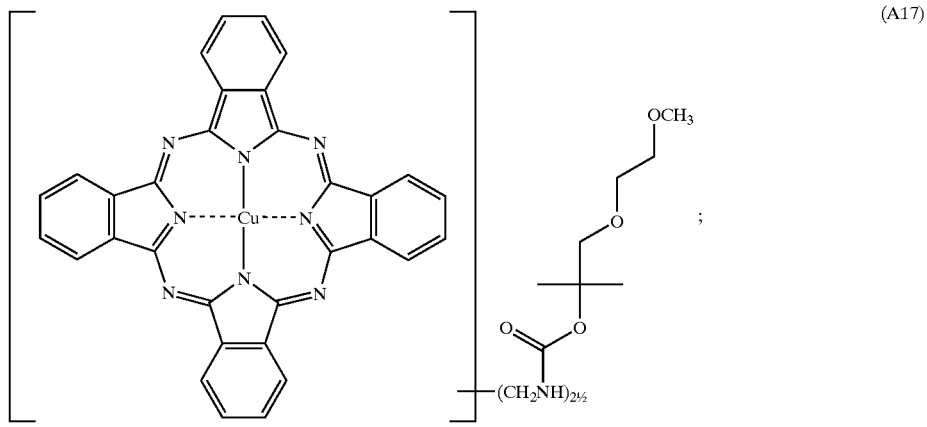
(A17)
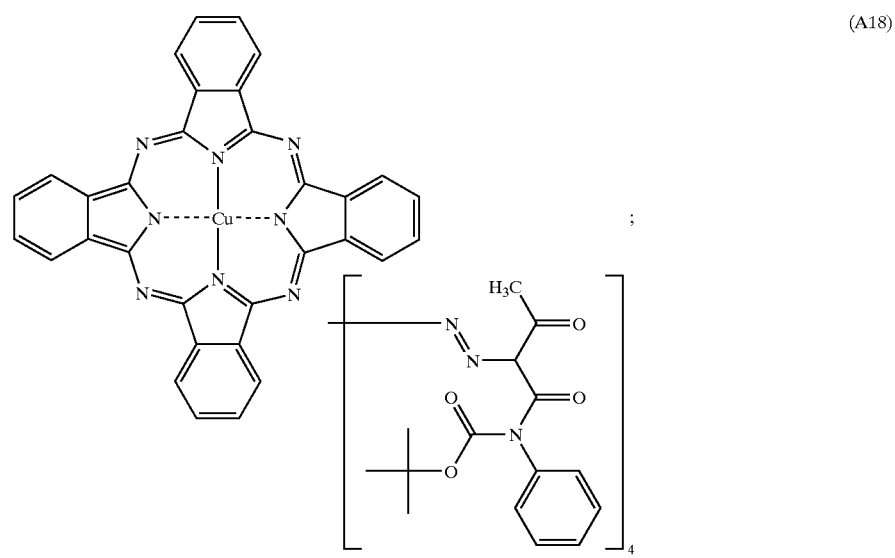
(A18)
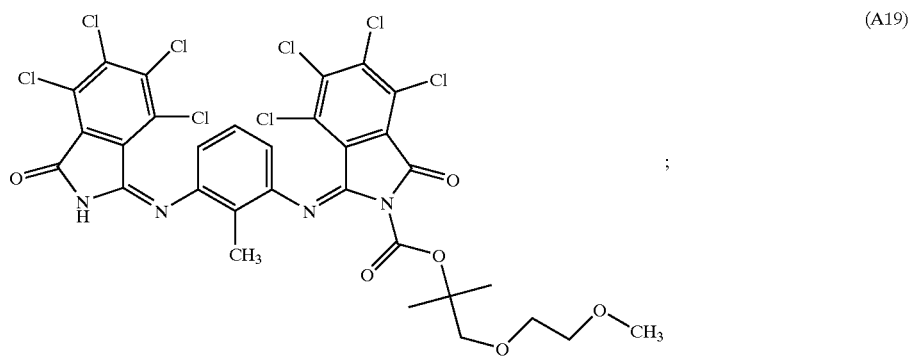
(A19)
| A20–A26 = mixtures containing following components (parts by weight): | | | | | |
|---|---|---|---|---|---|
| A20 (100) | A2 (25) | A5 (25) | A7 (25) | A12 (25) | — |
| A21 (100) | A2 (25) | A5 (25) | A9 (25) | A12 (25) | — |
| A22 (100) | A2 (12½) | A5 (25) | A7 (25) | A10 (12½) | A12 (25) |
| A23 (100) | A1 (50) | A6 (50) | — | — | — |
| A24 (100) | A9 (8) | A12 (77) | A16 (15) | — | — |
| A25 (100) | A12 (80) | A16 (20) | — | — | — |
| A26 (100) | A10 (50) | A16 (50) | — | — | — |

PREPARATION EXAMPLE A4

5.3 g of di-tert-butyldicarbonate are added to a suspension of 5 g of 3,6-bis-(4-diphenylamino-phenyl)-2,5-dihydro-pyrrolo[3,4-c]pyrrole-1,4-dione and 0.3 g of dimethylaminopyridine in 150 ml of tetrahydrofuran. After stirring overnight at room temperature, the reaction mixture was filtered through a small amount of kieselguhr. Addition of hexane to the residue followed by filtration provides 5.3 g of a violet compound having the above formula A4.

Analysis: calc.: C, 75.89%, H, 5.63%, N, 6.81%, O, 11.66%; found: C, 74.96%, H, 5.79%, N, 6.64%, O, 11.88%. Midpoint decomposition temperature: 184.7° C.; weight loss (calc.)=24.3%, weight loss (found)=26.06%.

PREPARATION EXAMPLE A6

8.8 g of di-(2-methoxy-1,1-dimethyl-ethyl)dicarbonate are added to a suspension of 3 g of unsubstituted quinacridone and 0.4 g of dimethylaminopyridine in 100 ml of tetrahydrofuran. After stirring overnight at room temperature, another 100 ml of tetrahydrofuran is added, and the reaction mixture is filtered through a small amount of kieselguhr, then through a small amount of silica gel. Evaporation of the filtrate and dissolution of the residue in dichloromethane, extraction with 3 portions of 100 ml of water, followed by drying of the organic phase over $Na_2SO_4$ and evaporation to dryness, affords 3.2 g of an orange compound having the above formula A6.

Analysis: calc.: C, 67.12%, H, 5.63%, N, 4.89%, O, 22.35%; found: C, 67.39%, H, 5.65%, N, 4.90%, O 22.31%. Midpoint decomposition temperature: 171.7° C.; weight loss (calc.)=45.4%, weight loss (found)=45.2%.

PREPARATION EXAMPLE A7

255 g of di-[2-(2-methoxy-ethoxy)-1,1-dimethyl-ethyl]dicarbonate are added dropwise to a suspension of 55 g of unsubstituted quinacridone and 5.3 g of dimethylaminopyridine in 750 ml of tetrahydrofuran. After stirring overnight at room temperature, the reaction mixture is filtered through a small amount of kieselguhr, and the filtrate is evaporated. After addition of n-hexane to the residue, filtration yields 40 g of an orange compound having the above formula A7.

Analysis: calc.: C, 65.44%, H, 6.10%, N, 4.24%, O, 24.22%; found: C, 65.25%, H, 6.48%, N, 4.13%, O, 24.26%. Midpoint decomposition temperature: 164.3° C.; weight loss (calc.)=52.7%, weight loss (found)=52.9%.

PREPARATION EXAMPLE A9

8.8 g of di-tert-amyldicarbonate are added to a suspension of 100 g of 3,7-bis-(2-oxo-1,2-dihydro-indol-3-ylidene)-3,7-dihydro-benzo[1,2-.b.;4,5-.b.']difuran-2,6-dione and 8.3 g of dimethylaminopyridine in 1250 ml of dimethylacetamide. After stirring overnight at room temperature, the reaction mixture is filtered through a small amount of kieselguhr and the filtrate is evaporated. Tetrahydrofuran and hexane are added to the residue, and filtration followed by drying provides 57.8 g (39% theory) of a dark compound having the above formula A9. Midpoint decomposition temperature: 133.1° C.; weight loss (calc.)=33.7%, weight loss (found)=28.6%.

PREPARATION EXAMPLE A18

In analogy to U.S. Pat. No. 2,351,119, tetraamino copper phthalocyanine is diazotised and the diazonium compound so obtained is coupled with acetoacetanilide. A suspension of 11 g of this tetraazo product in 120 ml of dimethylacetamide is charged with 0.86 g of N,N-dimethylaminopyridine and 15.2 g of di-tert-butyldicarbonate. After 18 h, the reaction mixture is filtered through some $MgSO_4$ and the filtrate is concentrated by evaporation to about 30 ml. The crude product is precipitated with water, collected by filtration, washed with 200 ml of hexane, dried and dissolved in dichloromethane. After filtration through silica gel, the product is again concentrated and some hexane is added.

The product is then subjected to filtration and dried, yielding 13.35 g (94% of theory) of a green powder.

UV/VIS (tetrahydrofuran): $\lambda_{max}$=682 nm, $\epsilon$=60689.

Elemental analysis [%]: theor.: C, 61.75; H, 4.73; N, 15.66; O, 14.31; Cu, 3.55; $C_{92}H_{84}N_{20}O_{16}Cu$, found: C, 61.06; H, 5.03; N, 15.28; O, 14.55; Cu, 3.60.

TGA (heating rate 10° C./min): turning point of the degradation=171° C.; loss in mass 25.6%.

Example 1

7 parts by weight of tetraethoxysilane, 1.3 parts by weight of nitric acid in 1.5 part by weight of water, 0.5 parts by weight of the product of formula (A10) in 89.89 parts by weight of water are mixed together to form a coating solution which is coated onto a cleaned glass plate by spin coating. After drying for 20 minutes at 80° C., the plate is heated to 200° C. for 20 minutes and an uniform violet coating is obtained.

Example 2

It is proceeded as in example 1, with the difference that the product of formula (A11) is used instead of the product of formula (A10). A similar uniform violet coating is obtained on the glass plate.

Example 3

It is proceeded as in example 2, with the difference that the homologue product of formula

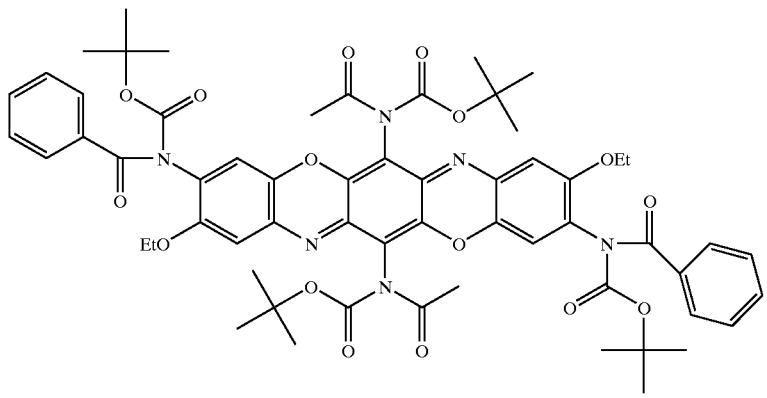

(A24)

is used instead of the product of formula (A11). The results are similar to those of example 2.

Example 4

It is proceeded as in example 1, with the difference that dioxane is used as a solvent instead of water. The results are similar to those of example 1.

Example 5

It is proceeded as in example 2, with the difference that dioxane is used as a solvent instead of water. The results are similar to those of example 2.

Example 6

It is proceeded as in example 3, with the difference that dioxane is used as a solvent instead of water. The results are similar to those of example 3.

Example 7

It is proceeded as in example 4, with the difference that the product of formula (A1) is used instead of the product of formula (A10). A uniform orange coating is obtained.

Example 8

It is proceeded as in example 4, with the difference that the product of formula (A14) is used instead of the product of formula (A10). A uniform bluish red coating is obtained.

Example 9

It is proceeded as in example 4, with the difference that the product of formula (A2) is used instead of the product of formula (A10). A uniform red coating is obtained.

Example 10

It is proceeded as in example 4, with the difference that the product of formula (A3) is used instead of the product of formula (A10). A uniform flame red coating is obtained.

Example 11

It is proceeded as in example 4, with the difference that the product of formula (A5) is used instead of the product of formula (A10). A uniform bluish red coating is obtained.

Example 12

It is proceeded as in example 4, with the difference that the product of formula (A12) is used instead of the product of formula (A10). A uniform yellow coating is obtained.

Example 13

It is proceeded as in example 4, with the difference that the product of formula (A13) is used instead of the product of formula (A10). A uniform yellow coating is obtained.

Example 14

It is proceeded as in example 4, with the difference that the product of formula (A15) is used instead of the product of formula (A10). A uniform brown coating is obtained.

Example 15

It is proceeded as in example 4, with the difference that the product of formula (A16) is used instead of the product of formula (A10). A uniform blue coating is obtained.

Example 16

It is proceeded as in example 4, with the difference that the product of formula (A17) is used instead of the product of formula (A10). A uniform blue coating is obtained.

Example 17

It is proceeded as in example 4, with the difference that the mixture (A20) is used instead of the product of formula (A10). A uniform black coating is obtained.

Example 18

It is proceeded as in example 4, with the difference that the mixture (A21) is used instead of the product of formula (A10). A uniform black coating is obtained.

Example 19

It is proceeded as in example 4, with the difference that the mixture (A22) is used instead of the product of formula (A10). A uniform black coating is obtained.

Example 20

It is proceeded as in example 4, with the difference that the mixture (A23) is used instead of the product of formula (A10). A uniform brown coating is obtained, which however has high transmission for blue, green and red light.

Example 21

15 parts by weight of tetraethoxysilane, 0.3 parts by weight of concentrated aqueous hydrochloric acid and 0.3 parts by weight of the product of formula

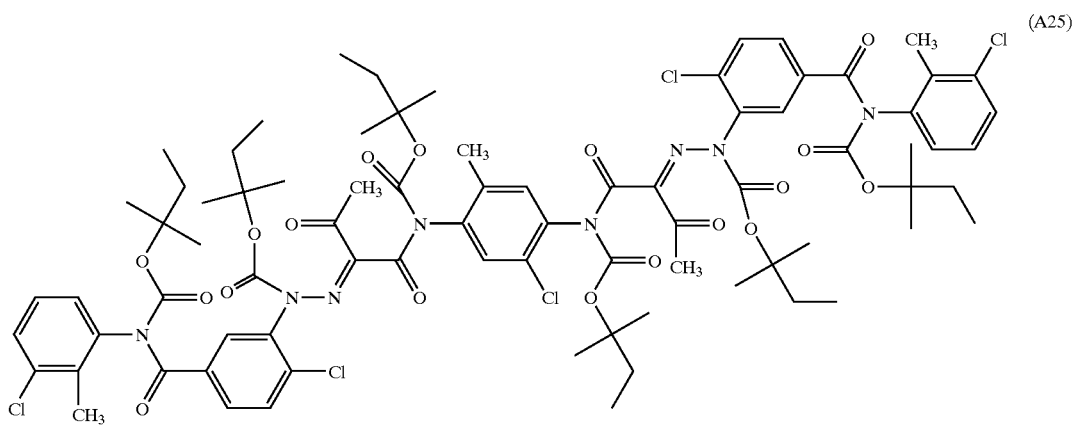

are dissolved into 1.2 parts of ethanol until slight agitation for 5 minutes. A clear solution is obtained, which is left standing at 23° C. for 12 hours. A gel is formed, which is heated to 150° C. for 180 minutes. The product is crushed in a mortar. Fine yellow particles are obtained, consisting of a silicon matrix in which particles of Pigment Yellow 93 are homogeneously embedded.

Example 22

It is proceeded as in example 20, with the differences that methyltributoxysilan is used instead of tetraethoxysilane, and 0.6 parts by weight instead of the product of formula (A25) of 0.3 parts by weight. The results are similar, however with a much higher colour saturation.

Example 23

0.3 parts by weight of the product of formula (A25) are dissolved into 15 parts by weight of tetraisopropyltitanate. A clear solution is obtained, to which 30 parts by weight of water are added dropwise. A stable gel is formed upon heating to 150° C., consisting of a titanium dioxide matrix in which particles of Pigment Yellow 93 are embedded.

Example 24

A mixture of 2.0 g tetraethoxysilane and 0.5 g of phenyl-triethoxysilane is dissolved into a mixture of 12.5 g of ethanol and 3.75 g of 1M-HCl. After 2 to 4 hours of hydrolysis, the reaction mixture is added dropwise to a solution of 0.40 g of the product of formula (A7) in 3.75 g of dimethylacetamide. After dilution with 20 g of isopropanol, the resulting solution is microfiltrated through a 0.45 μm filter, then spin-coated onto a glass substrate (first 10 s at 100 rpm, then 30 s at 500 rpm). The coated glass plate is dried for 2 min at 100° C., then heated further for 5 min at 200° C., whereby the colour changes from reddish orange to magenta.

Example 25

It is proceeded as in example 24, with the difference that the product of formula (A6) is used instead of the product of formula (A7). The colour changes from reddish orange to magenta.

Example 26

It is proceeded as in example 24, with the differences that cyclohexanone is used instead of dimethylacetamide, and that after drying, the coated glass plate is heated for 5 min at 250° C. The colour changes from reddish orange to violet.

Example 27

It is proceeded as in example 24, with the difference that 2-ethoxyethanol is used instead of ethanol. The colour changes from reddish orange to violet. The same results can be obtained with 2-n-butoxyethanol instead of 2-ethoxyethanol.

Example 28

It is proceeded as in example 27, with the difference that the coated glass plate is heated for 5 min at 180° C. The colour changes from reddish orange to violet. This shows that the use of 2-ethoxy-ethanol instead of ethanol surprisingly enables to obtain the desired violet colour of unsubstituted quinacridone advantageously at lower temperature.

Example 29

A mixture of 0.9 g tetraethoxysilane and 0.1 g of phenyl-triethoxysilane is dissolved into a mixture of 3 g of isopropanol, 1 g of 3-methoxy-propyl-acetate and 1.5 g of 1M-HCl. After 2 to 4 hours of hydrolysis, the reaction mixture is added dropwise to a solution of 0.20 g of the product of formula (A7) in 1.5 g of dimethylacetamide. After dilution with 8 g of isopropanol, the resulting solution is microfiltrated through a 0.45 μm filter, then spin-coated onto a glass substrate (first 5 s at 30 rpm, then 20 s at 500 rpm). The coated glass plate is dried for 2 min at 100° C., then heated further for 5 min at 250° C., whereby the colour changes from reddish orange to violet.

Example 30

It is proceeded as in example 26, with the differences that the product of formula (A4) is used instead of the product of formula (A7), and that after drying, the coated glass plate is heated for 5 min at 200° C. The colour changes from orange-yellow to violet.

Example 31

It is proceeded as in example 24, with the difference that 0.5 g of the mixture of formula (A25) is used instead of the product of formula (A7). The colour changes to green and matches closely that of conventional green glass such as used for wine or beer bottles.

Example 32

It is proceeded as in example 31, with the difference that 0.52 g of the product of formula (A24) is used instead of 0.5 g of the mixture of formula (A25). The colour changes to green, too.

Example 33

A mixture of 2.0 g tetraethoxysilane and 0.5 g of phenyltriethoxysilane is dissolved into a mixture of 12.5 g of isopropanol and 3.75 g of 1M-HCl. After 2 to 4 hours of hydrolysis, the reaction mixture is added dropwise to a solution of 0.50 g of the mixture of formula (A25) in 3.75 g of dimethylacetamide. After dilution with 20 g of isopropanol, the resulting solution is microfiltrated through a 0.45 µm filter. A 25 ml glass bottle is then immersed into this solution and slowly pulled out. After a short drain time, the bottle is heated to 200° C. A very transparent, attractive green coloration is obtained.

Example 34

It is proceeded as in example 33, with the difference that the product of formula (A12) is used instead of the mixture of formula (A25). A very transparent, greenish yellow coloration is obtained.

Example 35

It is proceeded as in example 33, with the difference that the product of formula (A19) is used instead of the mixture of formula (A25). A very transparent, yellow coloration is obtained.

Example 36

It is proceeded as in example 33, with the difference that the product of formula (A10) is used instead of the mixture of formula (A25). A very transparent, violet coloration is obtained.

Example 37

It is proceeded as in example 33, with the difference that the product of formula (A8) is used instead of the mixture of formula (A25). A very transparent, magenta coloration is obtained.

Example 38

It is proceeded as in example 33, with the difference that the product of formula (A2) is used instead of the mixture of formula (A25). A very transparent, red coloration is obtained.

Example 39

It is proceeded as in example 33, with the difference that the product of formula (A1) is used instead of the mixture of formula (A25). A very transparent, orange coloration is obtained.

Example 40

It is proceeded as in example 33, with the difference that 0.4 g of the mixture of formula (A26) is used instead of 0.5 g of the mixture of formula (A25). A very transparent, deep blue coloration is obtained.

Example 41

It is proceeded as in example 1, with the difference that the product of formula (A9) is used instead of the product of formula (A10). A uniform coating is obtained on the glass plate, the absorbtion maximum of which is at about 760–765 nm.

Example 42

2.0 g of diphenyldiethoxysilane are dissolved into a mixture of 7.5 g of ethoxy-ethanol and 0.25 g of water. After ½ to 1 hour of hydrolysis, the reaction mixture is mixed with a solution of 0.18 g of the product of formula (A7) and 1.2 g of polyhydroxystyrene (Maruca Lyncor™ resin, $M_w$=5300, Maruzen Petrochemicals/JP) in 7.5 g of ethoxy-ethanol. The resulting solution is diluted with 12 g of isopropanol and microfiltrated through a 0.45 µm filter, then spin-coated onto a glass substrate (first 5 S at 100 rpm, then 15 s at 400 rpm). The coated glass plate is dried for 2 min at 100° C., then heated further for 5 min at 200° C., whereby the colour changes from reddish orange to violet.

Example 43

It is proceeded as in example 42, with the difference that 24 g of isopropanol are used for dilution and the glass plate is heated for 5 min at 180° C. instead of 200° C. The results are similar.

Example 44

It is proceeded as in example 42, with the difference that a solution of 0.2 g Disperbyk 306 in 18 g of isopropanol are used for dilution. The results are similar, with the difference that the surface quality is improved.

Example 45

It is proceeded as in example 44, with the difference that Disperbyk® 333 is used instead of Disperbyk® 306. The results are similar.

Example 46

It is proceeded as in example 42, with the difference that a solution of 0.1 g of Disperbyk® 310 in 24 g of isopropanol is used for dilution. The results are similar, with the differences that the surface quality is improved and the colour is more violet, indicating a higher amount of the preferred β phase quinacridone.

What is claimed is:

1. A transparent, coloristically uniform vitreous material comprising a matrix of crosslinked liquid or dissolved transition metal atoms and effective pigmenting amounts of from 2 to 10 pigments selected from the group consisting of pigments of the quinacridone, anthraquinone, perylene, indigo, quinophthalone, indanthrone, isoindolinone, isoindoline, dioxazine, azo, phthalocyanine, diketopyrrolopyrrole and 3-methylidene-2,3-dihydro-indol-2-on pigment series.

2. A transparent, coloristically uniform vitreous material according to claim 1, which comprises no surfactant.

3. A transparent, coloristically uniform vitreous material according to claim 1, which optionally comprises a surfactant but comprises no dispersant.

4. A transparent, coloristically uniform vitreous material according to claim 1, which comprises polyhydroxystyrene.

5. A transparent, coloristically uniform vitreous material according to claim 1, comprising pigments of different pigment series.

6. A transparent, coloristically uniform vitreous material of claim 1, which is in the form of a from 0.1 to 3 µm thick film.

7. A transparent, coloristically uniform vitreous material of claim 4, which is in the form of a from 0.1 to 3 µm thick film.

8. A transparent, coloristically uniform vitreous material of claim 5, which is in the form of a from 0.1 to 3µm thick film.

9. A glass item coated with a transparent, coloristically uniform vitreous material of claim 1.

10. A glass article in the shape of a bottle coated with a transparent, coloristically uniform vitreous material of claim 1.

11. A display screen coated with a transparent, coloristically uniform vitreous material of claim 1.

12. A glass item coated with a transparent, coloristically uniform vitreous material of claim 4.

13. A display screen coated with a transparent, coloristically uniform vitreous material of claim 4.

14. A glass article in the shape of a bottle coated with a transparent, coloristically uniform vitreous material of claim 4.

15. A glass item coated with a transparent, coloristically uniform vitreous material of claim 5.

16. A display screen coated with a transparent, coloristically uniform vitreous material of claim 5.

17. A glass article in the shape of a bottle coated with a transparent, coloristically uniform vitreous material of claim 5.

18. A transparent, coloristically uniform vitreous material according to claim 1, comprising Color Index Pigment Yellow 13, Pigment Yellow 73, Pigment Yellow 74, Pigment Yellow 93, Pigment Yellow 94, Pigment Yellow 95, Pigment Yellow 109, Pigment Yellow 120, Pigment Yellow 128, Pigment Yellow 139, Pigment Yellow 151, Pigment Yellow 154, Pigment Yellow 175, Pigment Yellow 180, Pigment Yellow 181, Pigment Yellow 185, Pigment Yellow 194, Pigment Orange 31, Pigment Orange 71, Pigment Orange 73, Pigment Red 144, Pigment Red 166, Pigment Red 184, Pigment Red 185, Pigment Red 202, Pigment Red 214, Pigment Red 220, Pigment Red 221, Pigment Red 222, Pigment Red 242, Pigment Red 248, Pigment Red 255, Pigment Red 262, Pigment Red 264, Pigment Brown 23, Pigment Brown 41, Pigment Brown 42, Pigment Blue 25, Pigment Blue 26, Pigment Blue 60, Pigment Blue 64, Pigment Violet 29, Pigment Violet 32, Pigment Violet 37, 3,6-di(4'-cyano-phenyl)-2,5-dihydro-pyrrolo[3,4-c]pyrrole-1,4dione or 3phenyl-6-(4'-tert-butyl-phenyl)-2,5-dihydro-pyrrolo[3,4-c]pyrrole-1,4-dione.

19. A transparent, coloristically uniform vitreous material of claim 18 which is in the form of a from 0.1 to 3 μm thick film.

20. A transparent, coloristically uniform vitreous material according to claim 18, which comprises a surfactant.

21. A transparent, coloristically uniform vitreous material according to claim 18, which optionally comprises a surfactant but comprises no dispersant.

22. A transparent, coloristically uniform vitreous material according to claim 18, which comprises polyhydroxystyrene.

23. A transparent, coloristically uniform vitreous material according to claim 18, comprising pigment of different pigment series.

24. A glass item coated with a transparent, coloristically uniform vitreous material of claim 19.

25. A display screen coated with a transparent, coloristically uniform vitreous material of claim 18.

26. A glass article in the shape of a bottle coated with a transparent, coloristically uniform vitreous material of claim 19.

\* \* \* \* \*